United States Patent [19]

Deucher et al.

[11] Patent Number: 5,031,198
[45] Date of Patent: Jul. 9, 1991

[54] COMPOSITE DETECTOR MOUNTING RING FOR CT SCANNERS

[75] Inventors: Joseph S. Deucher, Lyndhurst; Anton Z. Zupancic, Kirtland; Charles A. Gardner, Ashtabula, all of Ohio

[73] Assignee: Picker International, Inc., Highland Heights, Ohio

[21] Appl. No.: 438,684

[22] Filed: Nov. 17, 1989

[51] Int. Cl.⁵ .................. H05G 1/64; H01J 35/10
[52] U.S. Cl. .......................... 378/4; 378/22; 378/189; 378/21; 378/15; 378/19
[58] Field of Search ............. 378/4, 11, 189, 19, 378/15, 193, 197, 21, 22, 10, 19

[56] References Cited

U.S. PATENT DOCUMENTS

| | | | |
|---|---|---|---|
| 4,464,776 | 8/1984 | Erker | 378/19 |
| 4,571,495 | 2/1986 | Distler et al. | 378/04 |
| 4,723,259 | 2/1988 | Amor et al. | 378/04 |
| 4,845,731 | 7/1989 | Vidmar et al. | 378/98 |
| 4,853,946 | 8/1989 | Elliott et al. | 378/04 |

Primary Examiner—Edward P. Westin
Assistant Examiner—Don Wong
Attorney, Agent, or Firm—Fay, Sharpe, Beall, Fagan, Minnich & McKee

[57] ABSTRACT

A deformable, inner ring (22) is mounted by spokes (24) to internal structure (26) of a CT scanner. A plurality of circuit boards (32) are bent in a circular arc that is concentric with an inner circular surface of the first ring and secured to the first ring such that the arcuate bend is maintained. Bending the flexible circuit boards into an arc stresses them such that they are cantilevered outward from the first ring, yet are held along the circular arc. A second ring (44) is connected to the outer ends of the circuit boards to assure that both ends of the circuit board are held in like diameter parallel circles. Brackets (52) hold the side edges of the circuit boards straight and linear. In this manner, the circuit boards on which radiation detectors (36) are mounted become a rigid, circular mounting assembly for the radiation detectors and provide the sole support for the second ring.

16 Claims, 5 Drawing Sheets

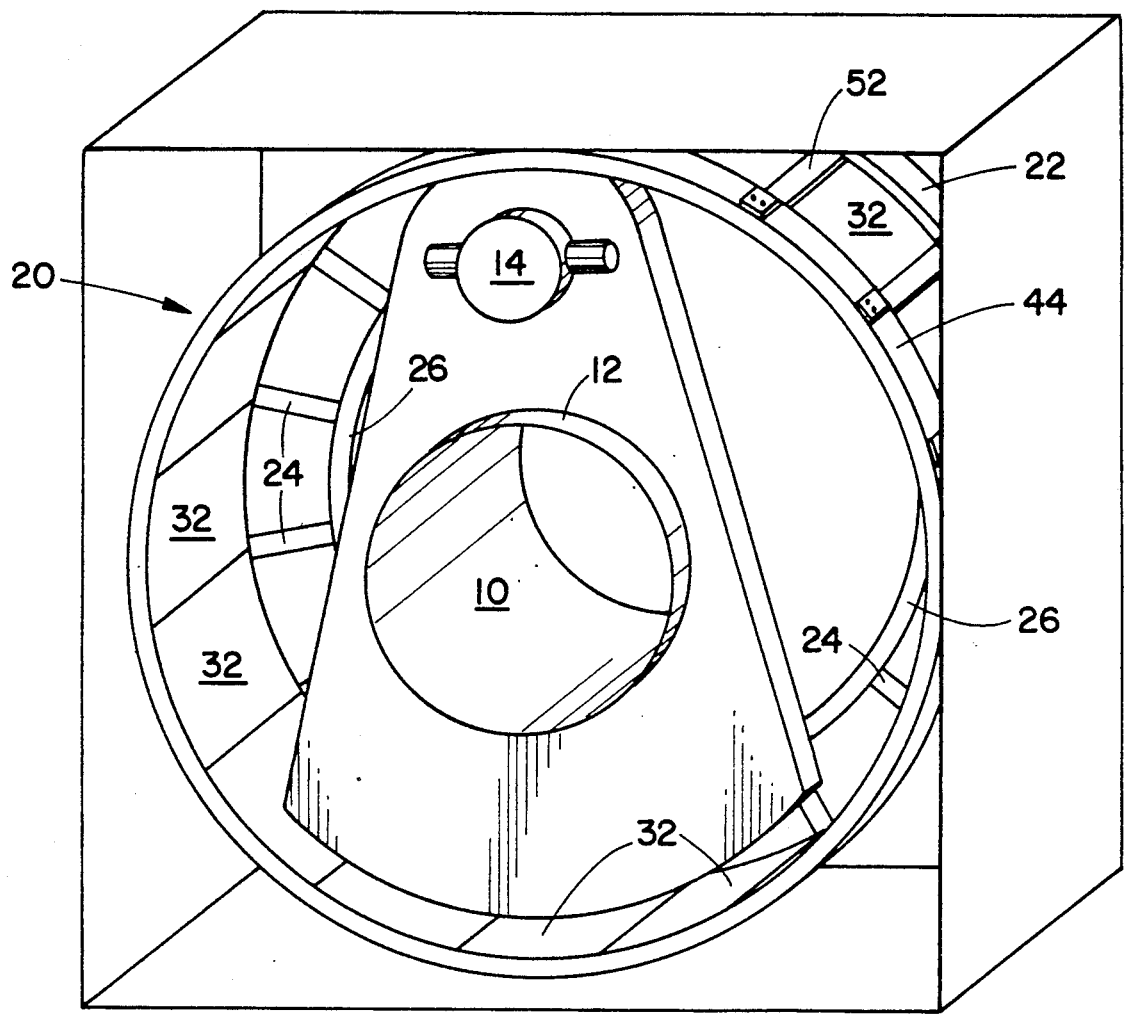
FIG. I 5,031,198

COMPOSITE DETECTOR MOUNTING RING FOR CT SCANNERS

BACKGROUND OF THE INVENTION

The present invention relates to the medical diagnostic arts. It finds particular application in conjunction with fourth generation CT scanners and will be described with particular reference thereto.

In fourth generation scanners, a continuous ring of x-ray detectors are mounted peripherally around the examination region. In order to accommodate the x-ray tube and other associated structure which conventionally rotates inside the ring, the detector ring is about one and a half meters in diameter.

Heretofore, a plurality of radiation detectors were mounted on each of a plurality of circuit boards. The circuit boards were constructed of conventional reinforced resin material a couple of millimeters thick which also supported various associated circuitry and electrical components. The circuit boards were flexible and could easily distort from the intended circular plane. Any deviation of the detectors from the prescribed circle could cause errors in radiation focus, image reconstruction, and otherwise degrade the resultant image.

In order to insure that the detectors conformed precisely to the prescribed circle, the circuit boards were securely mounted to a rigid, precision frame. For manufacturing convenience, the frame included twelve precast arcuate, tubular segments. The segments were precision machined such that they interconnected into a precise circle that would not flex or distort. This structure was mounted in the CT scanner cabinetry around the periphery of the detector circle and the circuit boards were mounted on the inner face thereof. Thus, the radiation struck the detectors before the cast supporting frame to avoid any interference with data collection.

Although the structures successfully held the detectors precisely in a prescribed circle, there were drawbacks. First, the precision machining of the inside surface, interconnecting edges, and the like to insure a precisely circular mounting surface for the detector boards was relatively expensive. Moreover, the pieces were cast relatively thick to assure rigidity and prevent flexing of the circuit boards. The segments proved relatively bulky and heavy in the crowded interior of a CT scanner.

In accordance with the present invention, a new and improved detector mounting arrangement is provided.

SUMMARY OF THE INVENTION

In accordance with the present invention, the circuit boards to which the detectors are mounted are themselves stressed structural members. More specifically, the circuit boards are mounted at one end to a ring member and arced transversely to conform to its curvature. The arcing of the circuit boards provide structural stability to hold the detectors in a circular array.

In accordance with a more limited aspect of the present invention, the opposite end of the circuit boards are connected together, e.g. with a second ring, to assure that both ends of the circuit board are arced with the same curvature. In a yet more limited aspect of the present invention, brackets are provided for supporting the edges of the circuit boards running between the two rings to assure that this edge remains linear.

In accordance with another aspect of the present invention, the mounting ring is flexible or distortable and is mounted to rigid structures of the CT scanner with a plurality of spokes. The spokes are configured and spaced at appropriate intervals to hold the distortable ring circular. Preferably, the mounting ring is a light weight composite material.

One of the advantages of the present invention is that it is compact and light weight.

Another advantage resides in its low cost and in the efficiency of manufacture.

Another advantage of the present invention is that it provides almost unlimited access to both sides of the circuit boards. This facilitates making electrical connections, provides greater air circulation for electrical component heat sinks, and the like.

Still further advantages of the present invention will become apparent to those of ordinary skill in the art upon reading and understanding the following detailed description of the preferred embodiments.

BRIEF DESCRIPTION OF THE DRAWINGS

The invention may take form in various parts and arrangements of parts. The drawings are only for purposes of illustrating a preferred embodiment and are not to be construed as limiting the invention.

FIG. 1 is a perspective view of a CT scanner assembly in accordance with the present invention;

DETAILED DESCRIPTION OF THE PREFERRED EMBODIMENT

A CT scanner defines a cylindrical patient receiving region 10 centrally therein. The patient receiving region is surrounded by a central, annular structure 12 about which an x-ray tube assembly 14 is rotatably mounted. Various electrical and hydraulic connections may be provided as part of the cylindrical structural member 12 or with interconnecting cables and hoses (not shown). In addition to an x-ray tube, the x-ray tube assembly commonly includes a high voltage power supply, tube cooling structures, and the like which have been deleted from FIG. 1 for simplicity of illustration.

Figure 1A:
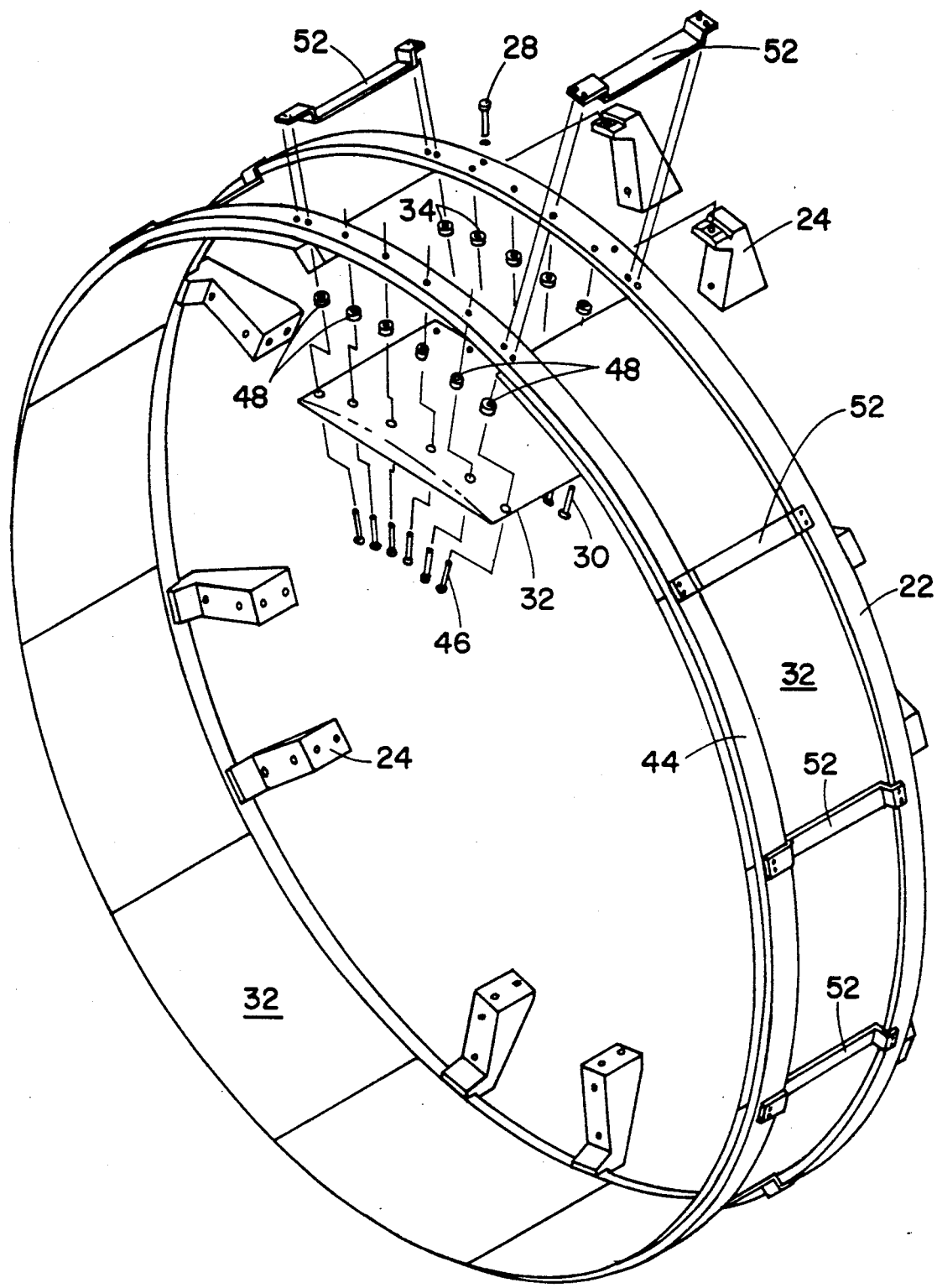
FIG. 1A is a perspective view of the circuit boards and circuit board mounting assembly of FIG. 1.
Figure 2:
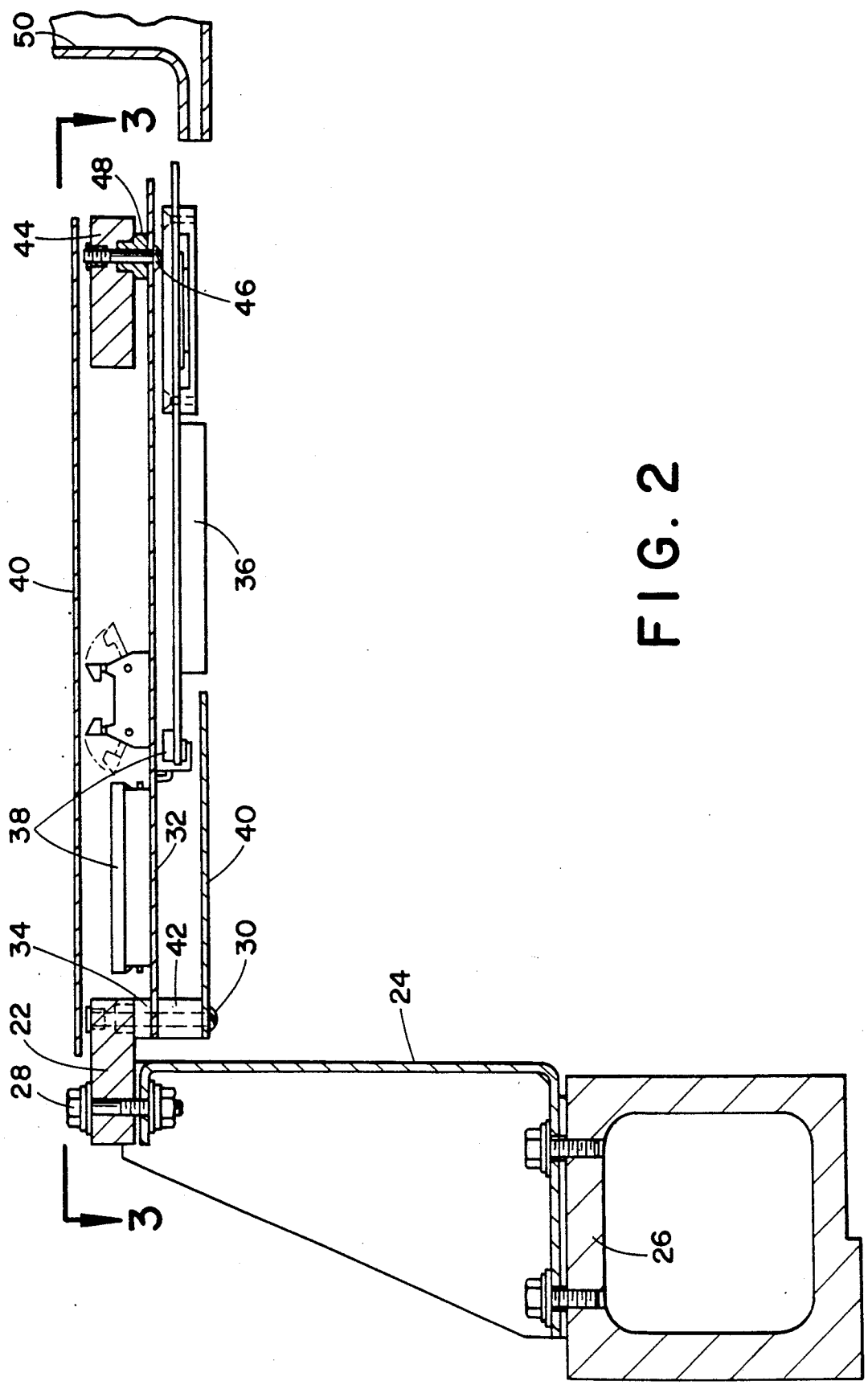
FIG. 2 is a transverse sectional view through the detector mounting assembly of FIG. 1.

A radiation detector mounting assembly 20 is mounted radially outside of the x-ray tube to define a circular detector mounting region. With continuing reference to FIG. 1 and further reference to FIGS. 1A-5, an inner circular ring 22 is mounted by a plurality of spokes 24 with a rigid structural portion 26 of the CT scanner or scanner housing. The inner mounting ring 22 of the preferred embodiment is configured of a fiber reinforced polymeric resin that is wound on a precision mandrel to insure a precisely circular inner diameter. The ring is predrilled with apertures at precisely determined locations to receive a mounting bolt 28 or other mounting means. With particular reference to FIG. 2, the relationships among the mounting bolt 28, mounting spoke 24, and inner mounting ring 22 are configured such that the roundness of the ring 22 can be adjusted, as necessary, to true the circular arc.

The inner mounting ring 22 is also predrilled with circuit board or mother circuit board mounting apertures to receive a mounting bolt or pin 30. A flexible, polymeric circuit board 32, also drilled with precisely positioned holes, receives the mounting pin or bolt 30. The pins clamp a first end of the board against a spacer 34 disposed between the mounting ring and the circuit board. The spacings between the holes along the board first end and in the ring are such that the circuit board is arced to conform to the radius or curvature of an inner surface of the ring 22. The inner surfaces of the spacers precisely define the circle to which the circuit boards are contoured. To facilitate assembly, the inner surface of the ring defines an exact circle and the spacers are of a consistent length.

The circuit board supports a plurality of detector modules 36 mounted directly thereon. Other associated electronic components 38 are also mounted to the board. Where appropriate, an electrical conductive shield 40 may be mounted by a second spacer 42 to shield the circuit components from the electrical interference.

By arcing the inner end of the circuit board 32 to conform to the inner mounting ring's radius of curvature, the heretofore flexible circuit board is stressed to become a rigid structure. To insure that the same curvature is carried along the length of the circuit board, a second mounting ring 44 is mounted directly to a second end of the circuit board. Again, a pin or bolt 46 and spacer 48 are provided. The inner surface of the outer ring and the length of the spacers are selected to define precisely the same circle as the inner ring and spacers. The outer mounting ring is mounted directly and only to the printed circuit board, not to other associated scanner structures. In this manner, the printed circuit boards 32 themselves are the bearing structure for supporting the outer ring 44. With reference to FIG. 2, a cooling duct 50 is mounted to the scanner, such as to front closures of the scanner to direct cooling air across the detector modules 36.

Figure 3:
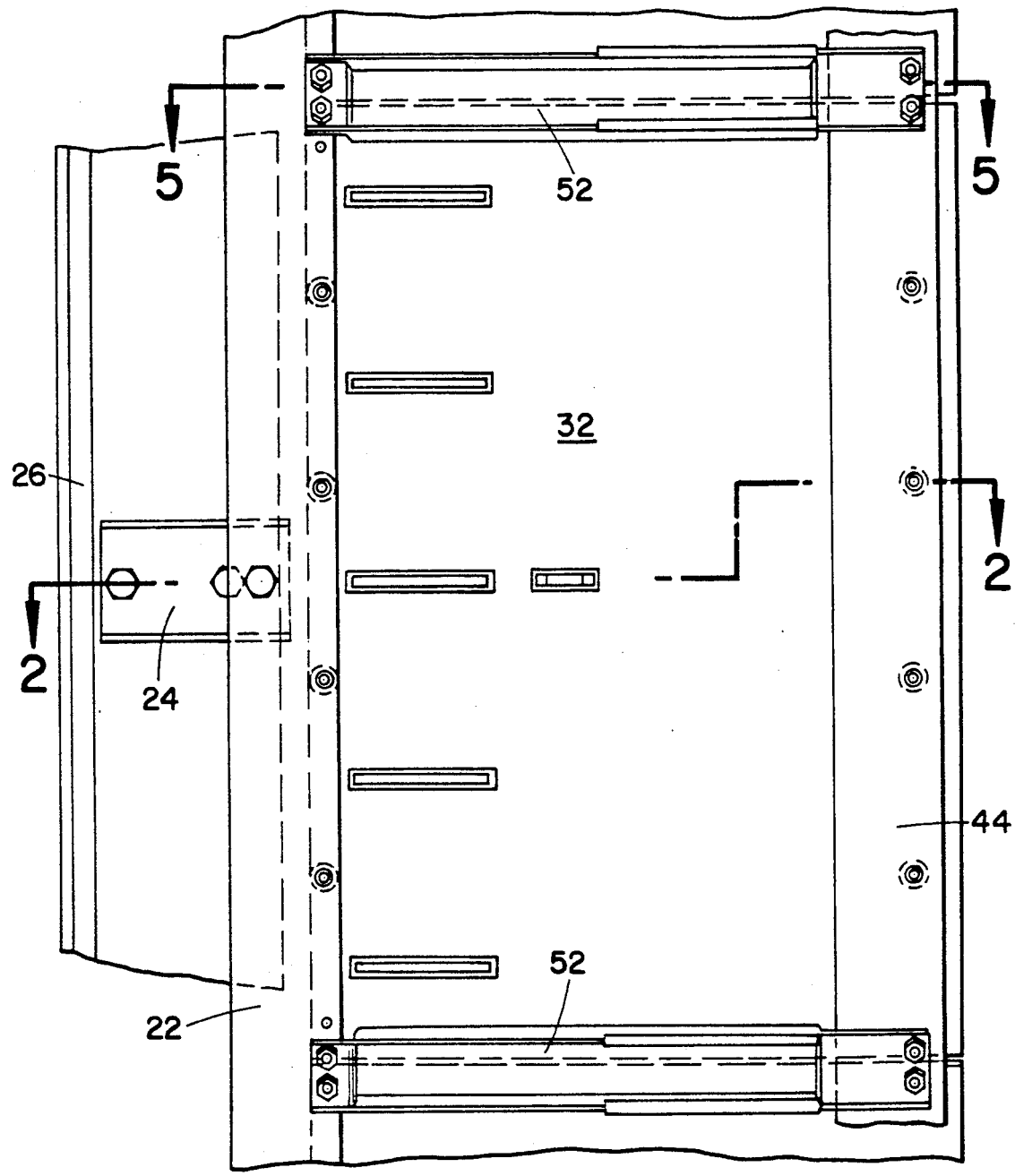
FIG. 3 is a bottom plane view of a circuit board and the associated mounting assembly.
Figure 4:
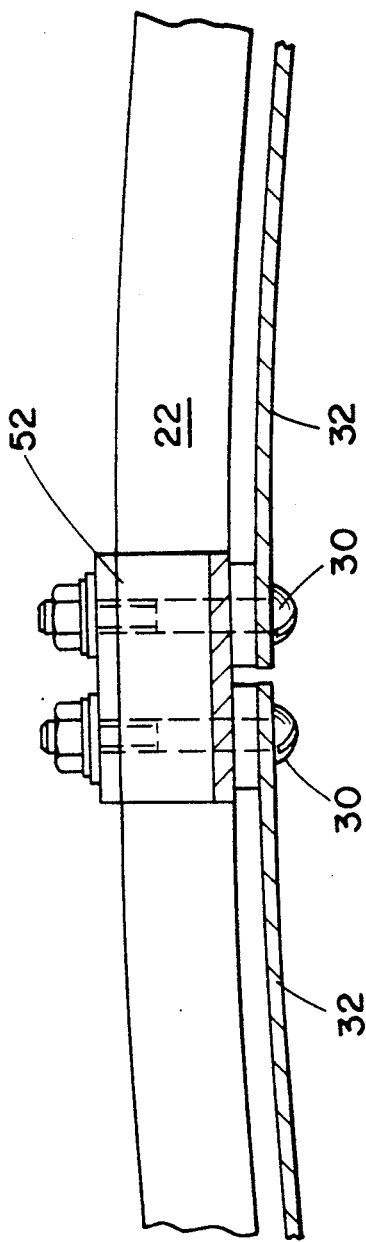
FIG. 4 is an end view in partial section of a portion of the circuit board and detector mounting ring assembly; and, FIG. 5 is a transverse sectional view like FIG. 2 but taken through a circuit board side edge supporting bracket.
Figure 5:
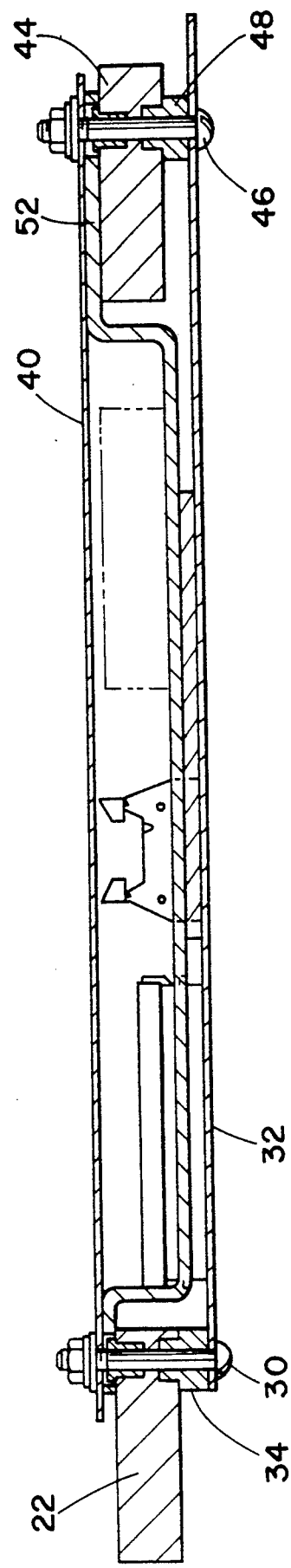

With particular reference to FIGS. 2 and 3, the inner and outer ends of the circuit boards are held to the arcuate configuration by the inner and outer rings. The other two sides of the circuit board extend linearly and parallel therebetween. In order to assure that the side edges of the circuit board stay linear without flexing, a plurality of edge support structures or brackets 52 are provided adjacent the sides of each circuit board. In the preferred embodiment, each circuit board spans 30° of arc carrying a large multiplicity of detectors. Twelve edge brackets are provided, one between each of the twelve circuit boards on the outer surface side thereof so as not to interfere with the radiation impinging upon the detectors. As illustrated in greater detail in FIG. 5, the edge brackets 52 are mounted to the outer surfaces of the rings but include portions extending downward to engage the circuit board side edges along substantially their entire length to hold the linear relationship. The electrical conductive shield 40 extends peripherally around the outside of the edge brackets, the rings, the circuit boards, and the like to limit electrical interference to the detectors.

The invention has been described with reference to the preferred embodiment. Obviously, modifications and alterations will occur to others upon reading and understanding the preceding detailed description. It is intended that the invention be construed as including all such alterations and modifications insofar as they come within the scope of the appended claims or the equivalents thereof.

Having thus described the preferred embodiment, the invention is now claimed to be:

1. A fourth generation CT scanner comprising:
   a light weight, deflectable first ring securely mounted to a scanner housing such that an inner surface thereof is fixed along a first circular path circumscribing an examination region;
   a plurality of flexible circuit boards each supporting radiation detection means, first ends of the circuit boards being mounted to the first ring inner surface and flexed into an arced cross-section to conform generally to the first circular path, whereby arcuately bending the circuit board renders it stiff and rigid;
   a lightweight, deformable second ring mounted to and supported by second ends of the circuit boards opposite the first ring for fixing the circuit board second ends along a second circular path parallel to the first circular path;
   a means for holding side edges of the circuit boards substantially linear and parallel between the first and second ends; and,
   a radiation source mounted for rotation around the examination region along a third circular path of lesser diameter than the first and second circular paths such that the radiation source moves between the examination region and the circuit boards.

2. The scanner as set forth in claim 1 wherein the first and second rings are constructed of a light weight composite.

3. The scanner as set forth in claim 1 further including spokes means for mounting the first ring to the CT scanner housing and an adjustable interconnection between the spokes and at least one of the first ring and the CT scanner housing for selectively adjusting curvature of the inner surface of the first ring.

4. The scanner as set forth in claim 1 further including a plurality of spacers disposed between the inner surface of the first ring and each circuit board such that the circuit boards are offset from and substantially concentric with the inner surface of the first ring.

5. In a CT scanner, a mounting assembly for mounting each of a plurality of flexible circuit boards that support radiation detectors, in a circular path around an examination region with a face of each circuit board facing the examination region, the assembly comprising:
   a means for fixing first ends of the circuit board flexed in an arc along a first circular path;
   a circular ring for fixing second ends of the circuit boards arced along a second circular path of substantially the same diameter as the first circular path, the circular ring for fixing the circuit board second ends being mounted with and supported by the circuit boards.

6. In a CT scanner, a mounting assembly for mounting each of a plurality of circuit boards that support radiation detectors, in a circular path around an examination region with a face of each circuit board facing the examination region, the assembly comprising:

a first circular ring mounted to the CT scanner for fixing first ends of the circuit board arced along a first circular path, the circuit boards being mounted to the first ring;

a means for fixing second ends of the circuit boards arced along a second circular path of substantially the same diameter as the first circular path, the means for fixing the circuit board second ends being supported by the circuit boards.

7. The assembly as set forth in claim 6 wherein the means for fixing the second ends of the circuit boards includes a second circular ring which is mounted to the circuit board second ends.

8. The assembly as set forth in claim 7 further including means for holding side edges of the circuit boards substantially straight and parallel.

9. The assembly as set forth in claim 7 wherein the means for holding the side edges of the circuit boards straight and parallel includes a bracket extending perpendicular to the first ring.

10. A fourth generation CT scanner comprising:

a flexible generally annular structure having a mounting surface of a preselected diameter;

an adjusting means for mounting and adjustably deflecting the flexible structure such that the mounting surface lies more precisely along a circle around a patient receiving region;

a plurality of flexible circuit boards flexed into conformity with segments of the circle and secured to the flexible annular structure mounting surface, the circuit boards supporting a plurality of radiation detectors, whereby as the adjusting means adjustably deflects the flexible annular structure, the flexible circuit boards are adjustably positioned adjusting the radiation detectors more precisely along a circle around the patient receiving region;

a source of radiation rotatably mounted inside of the circle for rotation around the patient receiving region.

11. A method of mounting radiation detectors in a fourth generation CT scanner, the method comprising:

mounting a flexible ring to the CT scanner;

adjusting the flexible ring until a mounting surface thereof is constrained to lie along a circle;

bending each of a plurality of circuit boards to which radiation detectors are mountable into conformity with a circularly arcuate segment and mounting the circuit boards to the circular ring mounting surface such that the circularly arcuate bending is maintained.

12. A method of mounting radiation detectors in a fourth generation CT scanner, the method comprising:

mounting a first flexible ring to the CT scanner such that an inner surface thereof is circular;

bending each of a plurality of circuit boards to which radiation detectors are mountable into conformity with a circularly arcuate segment and mounting the circuit boards to the circular ring inner surface such that the circularly arcuate bending is maintained;

mounting a second ring to the circuit boards such that the arcuate bending of the circuit boards is maintained between the first and second rings.

13. The method as set forth in claim 12 further including the step of constraining side edges of the circuit boards to extend linearly and parallel between the rings.

14. The method as set forth in claim 12 wherein the steps of mounting the circuit boards with the rings includes mounting the circuit board's adjacent innermost surfaces of the rings.

15. The method as set forth in claim 14 further including forming the first and second rings by wrapping on a precision, circular mandrel such that the first and second rings innermost surfaces are of precisely the same diameter.

16. A CT scanner comprising:

a light weight, deformable first ring securely and nonrotatably mounted to a CT scanner housing;

a plurality of flexible, flat circuit boards each supporting a radiation detection means, a first end of each circuit board being flexed into an arc and mounted to the first ring;

a second ring mounted to and supported only by second ends of the circuit boards to hold the circuit board second ends flexed;

a radiation source mounted for rotation along a path inside of the circuit boards and the first and second rings for directing a beam of penetrating radiation toward the radiation detection means.

* * * * *